US010111995B2

(12) United States Patent
Breedon et al.

(10) Patent No.: US 10,111,995 B2
(45) Date of Patent: Oct. 30, 2018

(54) ELECTROACTIVE ACTUATORS

(71) Applicants: The Nottingham Trent University, Nottingham (GB); Nottingham University Hospitals NHS Trust, Nottingham (GB)

(72) Inventors: Philip Breedon, Nottingham (GB); Fergal Coulter, Nottingham (GB); David Richens, Nottingham (GB)

(73) Assignees: THE NOTTINGHAM TRENT UNIVERSITY, Nottingham (GB); NOTTINGHAM UNIVERSITY HOSPITALS NHS TRUST, Nottingham (GB)

( * ) Notice: Subject to any disclaimer, the term of this patent is extended or adjusted under 35 U.S.C. 154(b) by 139 days.

(21) Appl. No.: 14/897,816

(22) PCT Filed: Jun. 12, 2014

(86) PCT No.: PCT/GB2014/051813
§ 371 (c)(1),
(2) Date: Dec. 11, 2015

(87) PCT Pub. No.: WO2014/199167
PCT Pub. Date: Dec. 18, 2014

(65) Prior Publication Data
US 2016/0144091 A1 May 26, 2016

(30) Foreign Application Priority Data

Jun. 13, 2013 (GB) .................................. 1310578.8

(51) Int. Cl.
*A61M 1/10* (2006.01)
*A61M 1/12* (2006.01)
(Continued)

(52) U.S. Cl.
CPC ......... *A61M 1/1046* (2013.01); *A61F 2/0036* (2013.01); *A61M 1/107* (2013.01);
(Continued)

(58) Field of Classification Search
CPC .... A61M 1/122; A61M 1/107; A61M 1/1058; A61F 2/0031
See application file for complete search history.

(56) References Cited

U.S. PATENT DOCUMENTS

| 4,015,590 A | 4/1977 | Normann |
|---|---|---|
| 4,195,623 A | 4/1980 | Zeff |

(Continued)

FOREIGN PATENT DOCUMENTS

| EP | 0192574 | 5/1989 |
|---|---|---|
| WO | 20140199167 | 12/2014 |

OTHER PUBLICATIONS

Abramovitch H, Burgard M., Edery-Azulay L, Evans K.E., Hoffmeister M., Miller W., Scarpa F., Smith C.W., Tee K.F.,(2010) Smart tetrachiral and hexachiral honeycomb: Sensing and impact detection. Composites Science and Technology vol. 70, Issue 7, Jul. 2010, pp. 1072-1079.

(Continued)

*Primary Examiner* — Bruce E Snow
(74) *Attorney, Agent, or Firm* — Allan Watts PLLC

(57) ABSTRACT

The invention relates to actuators based on electroactive polymeric materials for use in pumping fluids or in other applications where a contractile actuation is required, in particular, although not necessarily exclusively, for use in vascular pulsation devices such as a variable aortic tension device. Embodiments disclosed include an actuator comprising: an inner tubular structure; an outer tubular structure surrounding the inner tubular structure and comprising a plurality of layers of a dielectric elastomeric material and a (Continued)

tubular elastic support structure, the elastic support structure configured to maintain a pre-stress in the layers of the dielectric elastomeric material, wherein the outer tubular structure is configured to contract in a radial direction around the inner tubular structure upon application of an actuation voltage signal across the dielectric elastomeric material layers.

3 Claims, 6 Drawing Sheets

(51) Int. Cl.
*A61F 2/00* (2006.01)
*B29C 64/106* (2017.01)
*B33Y 10/00* (2015.01)
*B33Y 80/00* (2015.01)
*B29K 83/00* (2006.01)
*B29L 9/00* (2006.01)
*B29L 31/00* (2006.01)

(52) U.S. Cl.
CPC ........... *A61M 1/122* (2014.02); *B29C 64/106* (2017.08); *A61F 2250/0001* (2013.01); *A61M 1/1001* (2014.02); *A61M 1/1005* (2014.02); *A61M 1/1037* (2013.01); *A61M 1/1043* (2014.02); *A61M 1/1058* (2014.02); *A61M 1/1086* (2013.01); *A61M 2205/0283* (2013.01); *A61M 2207/00* (2013.01); *B29K 2083/00* (2013.01); *B29L 2009/005* (2013.01); *B29L 2031/7534* (2013.01); *B33Y 10/00* (2014.12); *B33Y 80/00* (2014.12)

(56) References Cited

U.S. PATENT DOCUMENTS

| | | | |
|---|---|---|---|
| 4,697,574 A | 10/1987 | Karchner | |
| 4,733,652 A | 3/1988 | Kantrowitz | |
| 6,030,335 A | 2/2000 | Franchi | |
| 6,210,318 B1 | 4/2001 | Lederman | |
| 7,064,472 B2* | 6/2006 | Pelrine | A61M 5/142 310/324 |
| 7,347,811 B2 | 3/2008 | Peters | |
| 8,777,833 B2 | 7/2014 | Peters | |
| 2004/0076633 A1 | 4/2004 | Thomsen | |
| 2004/0230090 A1* | 11/2004 | Hegde | A61M 1/1053 600/18 |
| 2006/0074325 A1* | 4/2006 | Karo | A61B 5/02141 600/494 |
| 2007/0248614 A1 | 6/2007 | Thomsen | |
| 2016/0144091 A1 | 5/2016 | Breedon | |

OTHER PUBLICATIONS

Alderson A, Alderson K.L., Attard D., Evans K.E., Gatt R., Grima J.N., Miller W., Ravirala N., Smith C.W., Zied K. (2010) Elastic constants of 3-, 4- and 6-connected chiral and anti-chiral honeycombs subject to uniaxial in-plane loading. Composites Science and Technology 70 (2010) 1042-1048.
Araomi O.A., Conn A.T., Ling C.S, Rossiter J.M., Vaidyanthan R, Burgess S.C. (2011) Spray deposited multilayer dielectric elastomer actuators. Sensors and Actuators A : Physical, vol. 167, Issue 2, Jun. 2011, pp. 459-467.
Barnard SP, Hasan A, Forty J, Hilton CJ, Dark JH. (1995) Mechanical ventricular assistance for the failing right ventricle after cardiac transplantation. Eur. J. Cardiothorac., 9 ( 6 ), 297.
Carpi, F., Rossi, D.D., (2005) , Improvement of electromechanical actuating performances of a silicone dielectric elastomer by dispersion of titanium dioxide powder, Dielectrics and Electrical Insulation, IEEE Transactions on, vol. 12, No. 4, pp. 835-843, Aug. 2005.
Carpi F, Chiarelli P, Mazzoldi A, De Rossi D (2003) "Electromechanical characterisation of dielectric elastomer planar actuators: comparative evaluation of different electrode materials and different counterloads" Sensors and Actuators A 107 85-95.
Carpi, De Rossi, Kornbluh, Pelrine & Sommer-Larsen Editors. (2008) "Electromechanical Transduction effects in dielectric elastomers : Actuation, Sensing, Stiffness Modulation and Electric Energy Generation." Chapter 1 (Springer, 2008).
Chuc N.H, Thuy D.V, Park J., Kimd., Koo, J, Lee Y., Nam J.D., Choi H.R. (2008) A dielectric elastomer actuator with self-sensing capability. EAPAD (2008) Proc of SPIE vol. 6927,69252A.
Dedhia J.D, Kotemane N.C., Ahmed A.B., (2008) Intra Aortic Balloon Pump (IABP): Past, Present and Future. Indian Journal of Anaesthesia 2008; 52 (4):387-396.
Delille R, Urdaneta M, Hsieh K, Smela E. (2009) Compliant electrodes based on platinum salt reduction in a urethane matrix. Smart Materials and Structures 16 S272-S279).
Furman S, Attai L, Parker B. Cardiac support by periaortic diastolic augmentation. NY State J Medicine. 1970; 70: 1964-1969.
Furman S, Whitman R, Stewart J, Parker B, McMullen M. Proximity to aortic valve and unidirectionality as prime factors in counterpulsation effectiveness. Trans Am Soc Artif Int Organs. 1971; 17: 153-159.
Ganau A, Devereux RB, Pickering TG, Roman MJ, Schnall PL, Santucci S, Spitzer MC, Laragh JH. (1990). Relation of left ventricular hemodynamic load and contractile performance to left ventricular mass in hypertension. Circulation , 81 ( 1 ), 25-36.
Guest, S.D & Pellegrino, S., (1994) The folding of triangulated Cylinder, Part I, Geometric considerations, J. of Appl. Mech. 61,773-777 (1994).
Glazzard M., and Breedon P, (2013), Weft-knitted auxetic textile design, Status Solidi Journal (accepted subject to revisions).
Hu, L, Yuan, Wei, B., Gruner, P. Pei G, (2009) Highly stretchable, conductive, and transparent nanotube thin films, Applied Physics Letters , vol. 94, No. 16, pp. 161108-161108-3, Apr. 2009.
Keplinger et al.,Stretchable, transparent, ionic conductors, Science 341(6149): 984-987.
Kofod, G. Paajanen M, Bauer S (2006) Self-organized minimum-energy structures for dielectric elastomer actuators (2006) Appl Phys A 85, 141-143.
Kofod G. (2001) "Dielectric Elastomer Actuators" PhD Thesis—The Technical University of Denmark.
Legget, M.E. William S. Peters, W.S., Milsom F.P., Clark, J.S., West, T.M, French, R.L. and Merry, A.F. (2005) . Extra-Aortic Balloon Counterpulsation : An Intraoperative Feasibility Study. Circulation. Aug. 30, 2005;112(9 Suppl):I26-31.
Madden J.D.W. (2008) Dielectric elastomers as high performance electroactive polymers. In Fedrico Carpi, Danilo De Rossi, Roy Kombluh, Ronald Perline, and Peter Sommer-Larson, editors, Dielectric Elastomers as Electromechanical Transducers, chapter 2. Elsevier, 2008.
McKenzie A.C., Calius E.P., Anderson I.A. (2008) Electric field around a dielectric elastomer actuator in proximity to the human body. EAPAD (2008) Proc of SPIE vol. 6927, 69252A.
Mulgaonkar A., Kornbluh R., Herr H. (2008) A New Frontier for Orthotics and Prosthetics: Application of Dielectric Elastomer Actuators to Bionics, Dielectric Elastomers as Electromechanical Transducers: Fundamentals, Materials, Devices, Models & Applications of an Emerging Electroactive Polymer Technology. Elsevier; 2008.
Nguyen HC, Doan VT, Park J, Koo JC, Lee Y, Nam JD and Choi HR. (2009) "The effects of additives on the actuating performances of a dielectric elastomer actuator" Smart Mater. Struct. 18.
Raman, J., Loor G., London M., Jolly N., (2010) Subclavian Artery Access for Ambulatory Balloon Pump Insertion. Ann Thorac Surg. Sep. 2010;90(3):1032-4. doi: 10.1016.
Song, Xinwei; Throckmorton, Amy L. Untaroiu, Alexandrina Patel, Sonna; Allaire, Paul E.; Wood, Houston G. Olsen, Don B. (2003) Axial Flow Blood Pumps. ASAIO Journal: Jul. 2003—vol. 49—pp. 355-364.
Sutherland, K (2010) Bridging the quality gap: heart failure. The Health Foundation (Pub).

(56) References Cited

OTHER PUBLICATIONS

Urdaneta MG, Delille, R., Smela E. (2007) Stretchable Electrodes with High Conductivity and Photo Patternability Advanced materials, vol. 19, Issue 18, pp. 2629-2633, Sep. 2007.

Yuan, W., Hu, L., Ha, S., Lam T. Cruner G, Pei Q (2008) Self Clearable Carbon Nanotube Electrodes for Improved performance of Dielectric Elastomer Actuators. EAPAD Proc of SPIE vol. 6927. Bar-Cohen J. Ed.

* cited by examiner

ELECTROACTIVE ACTUATORS

CROSS-REFERENCE TO RELATED APPLICATIONS

This application is a national stage application under 35 U.S.C. 371 of and claims priority to International Application No. PCT/GB2014/051813, filed Jun. 12, 2014, which claims priority to Great Britain Application No. 1310578.8 filed on Jun. 13, 2013. International Application No. PCT/GB2014/051813 and Great Britain Application No. 1310578.8 are incorporated herein by reference.

FIELD OF THE INVENTION

The invention relates to actuators based on electroactive polymeric materials for use in pumping fluids or in other applications where a contractile actuation is required, in particular although not necessarily exclusively for use in vascular pulsation devices such as a variable aortic tension device.

BACKGROUND

The current state of the art of implantable cardiac assist technology consists of either a cannula-coupled constant flow pump which heavily supplements the left ventricle, or an implantable intra-aortic balloon.

Intra-Aortic Balloon Pumps (IABPs) such as those described in U.S. Pat. No. 6,210,318 and EP 0192574 (also published as U.S. Pat. No. 4,697,574) are well established technology which comprise of a mechanical device that sits at the top of the descending aorta. The device counterpulsates synchronously but in anti-phase with the heartbeat. This has the effect of increasing coronary blood flow and reducing afterload (known as aortic tension). The system works by mounting an inflatable polyethylene or silicone balloon on a catheter just distal to the left subclavian artery. A pneumatic (helium or carbon dioxide) line is then run through the arterial system, having entered the body through the skin (commonly at the groin femoral artery). During the hearts' diastolic (relaxing) phase the balloon is inflated, which serves to increase retrograde blood flow to the coronaries by displacing around 40 ml of blood from the balloon site, approximately half of which passess retrograde towards the aortic valve. Of this displaced blood, only 5 ml of displacement travels down the coronary arteries, with the rest perfusing the arteries that sit between the ascending and descending aorta. The retrograde coronary blood flow increases oxygen supply to the muscle of the heart (the myocardium). When the systolic (contracting) heart phase takes place the balloon deflates very quickly. This sudden release of pressure in the aorta offloads the ventricle, decreasing the work of the heart in systole and thereby the myocardial oxygen demand. This change in the myocardial oxygen supply and demand reverses the previous imbalance in the myocardium and thereby increases cardiac output.

Indications for an IABP include cardiogenic shock, intractable angina, and counteracting a low cardiac output after a coronary artery bypass graft (CABG). The IABP is amongst the most widely used bio-mechatronic human dynamic support systems.

Intra-aortic balloon pump insertion is traditionally performed through the femoral artery in the groin. However, this restricts the patient to bed rest, and prolonged implantation can be associated with infections in the groin crease and generalised sepsis from contamination of the balloon catheter from microorganisms present at the insertion site. Raman et al. (2010) describe a technique of insertion of a balloon pump through the subclavian artery, which allows the patient to ambulate. This technique can also be performed under local anaesthesia in the cardiac catheterization laboratory. IABPs cannot be deployed for long periods of time because of the risks of sepsis, arterial wall trauma, ischaemia in the relevant limb distal to the insertions site, thrombolic complications from exposure of the blood to a large surface area of foreign material, clotting abnormalities secondary to platelet consumption and device failure since their thin silicone balloons are prone to rupture.

In a chronic situation, where an intra-aortic balloon pump cannot be used (for the reasons described above), an extraaortic balloon pump (EABP) may be used. EABPs such as those described in WO 02/24255, WO 2004/045677 and U.S. Pat. No. 4,733,652 address some of the problems associated with IABPs, being attached to the external surface of the aorta rather than being implanted within the aorta. These non-blood-contacting cuffs works in a similar manner to the IABP, though they surround the aorta and rely on external compression to displace blood. The insertion point through the skin can be variable (for example near the subclavian artery) due to the devices external arterial design. This allows for greater freedom of mobility for the patient, but the problem remains that a percutaneous tube is required (Legget et al, 2005). The EABP (Sunshine Heart C-Pulse) has not seen widespread clinical acceptance, where only a small number have ever been implanted worldwide. This is partly due to the restricted space available for installation around the ascending aorta. More significantly, the design depends on the natural ascending aorta to still be in place. At a time when such a device might be implanted, the aorta itself will tend to be diseased, becoming hardened through atherosclerosis and likely suffering from a narrowing of bore (stenosis). The compression of a hardened and constricted aorta has been found to be contraindicated.

Other disadvantages of EABPs can include increasing atheromous emboli (accumulation of plaque inside the aorta) through interaction with the aortic wall and migration and interference with neighbouring structures e.g. erosion of the pulmonary artery or lungs. That said, the placement around the ascending aorta means the device need only displace 10 ml of blood (5 ml in either direction) to achieve the equivalent effect as a 40 ml displacement of an IABP in the descending aorta. This is due to the retrograde losses into the three ascending arteries on the aortic arch being negated.

Other technologies which similarly augment blood flow using balloon pumps include a balloon pump for insertion into the descending aorta described in U.S. Pat. No. 6,030,335 but this device has a rigid outer body which precludes its implantation at the optimal position in the lower ascending aorta where pumping effect is optimised. Conduit mounted balloon pumps described in U.S. Pat. No. 4,195,623 and U.S. Pat. No. 4,015,590 are similarly non-optimally positioned. As far as the inventors are aware, these devices are not currently in clinical use.

In experimental studies by Furman et al., (1970, 1971) it was shown that diastolic counterpulsation is more effective at the level of the ascending aorta, for a number of reasons. Firstly, the closer the diastolic pulse wave generation is to the aortic valve, the more accurately counterpulsation can be timed to ventricular systole without conflict between the ventricular wavefront progressing distally from the aortic valve and the assist wave progressing proximally. Thus, proximity to the aortic valve allows better synchrony of the cardiac cycle to counterpulsation. Also, pulse propagation is minimized, reducing counterpulsation efficiency loss.

Substantial investigation has been carried out into different methods for cardiac assist devices. EABP and IABP have improved substantially in terms of reliability and thus increased patient survival rates. Aortic Balloon Pumps (ABP) are the most common mechanical circulatory assistance device used today (Dedhia et al, 2008). FIG. 1*a* illustrates the main components of the heart in a schematic cutaway view. FIG. 1*b* illustrates an IABP in situ within the aorta, showing the IABP inflated during the diastolic phase. FIG. 1*c* illustrated an EABP in situ around the aorta, showing the EABP inflated during the diastolic phase. By inflating and thus occluding (blocking fully or partially) the aorta during the diastolic (relaxing) phase of the heartbeat, the blood pressure is proximal to the balloon in the ascending aorta. This increases coronary blood flow. As the heart enters the systolic (contracting) phase, the balloon is released, which allows blood to rush into the aorta. This offloads the contraction of the heart as it displaces blood into the circulation. The pump therefore works by increasing coronary artery blood flow and reducing the afterload on the heart.

Other types of VAD include numerous types of pumps known as axial flow pumps, which work by increasing the blood follow in parallel with the natural heart. These tend to provide constant flow rather than being pulsatile in their pumping action. Problems with such devices include the pumps being solid and bulky, and not always easily fitting in the chest cavity of smaller human torso. Such pumps use a lot of power to rotate between 8,000-12,000 revolutions per minute, and so require bulky external battery packs. All feature similar power consumption (~10 W), have percutaneous cables that protrude through the abdominal wall, and require ~2.5 Kg control unit plus lithium-ion or lead acid batteries. The high speed impellors also have a tendency to damage red blood cells, or cause hemolysis (a separation of red blood cells and haemoglobin). A further problem is that regions of stagnant flow can result in thrombus formations.

There are numerous axial flow pumps (AFP), incorporating impellers of varying geometry. Amongst the most popular (Xinwei, 2003), at least in US markets, where figures are most readily available, are Medtronic Hemopump, Micromed DeBakey, Jarvik 2000 and Streamliner. These designs vary mostly around impeller and casing size, speed of rotation and impeller geometry. They generally work in parallel with the natural heart—the left ventricle still pumps in pulsatile fashion, while the AFPs output a continuous flow of 5-7 L/min at 13 kPa pressure. Variations in design include the Jarvik, which is small enough to sit inside the ventricle, making it quieter and lighter than others. The Streamliner features a magnetic levitation impeller which reduces friction, thus heating the blood and also reduces non-encapsulated (wetted) components. It also increases complexity of control significantly, requiring constant monitoring and shifting of the magnetic field, to keep the impeller aligned. The DeBakey has a specially designed low shear geometry (designed in conjunction with NASA).

There are a number of negative responses from the body arising from the use of axial flow pumps. These stem from the introduction of a constant blood flow. Kidney function can deteriorate, reflexes are reduced and the function of the endocrine system is sometimes altered. These devices are designed to run in parallel with the heartbeat, thus a small pulsatile flow is maintained. While this serves to reduce these issues, full pulsatile flow would be preferable.

With all types of ventricular assist devices, the machines used to support such intervention either cannot be implanted inside the body or can only be implanted for a few days. The therapy also inevitably involves the patient being bedbound in hospital whilst being attached to a machine that is partially implanted into the patient, involving the need for transdermal lines and catheters. On average there are 754.5 hospital bed days per patient utilised from primary diagnosis (Sutherland et al, 2010). With an ever increasing risk of hospital born infections such as MRSA and *C. Diff*, there is an absolute need to design a fully implantable system which will give the patient the same level of mechanical heart assistance without needing prolonged periods confined in a hospital environment. Such a system is not currently available.

It is an object of the invention to address one or more of the above mentioned problems.

SUMMARY OF THE INVENTION

In accordance with a first aspect of the invention there is provided an actuator comprising:
  an inner tubular structure;
  an outer tubular structure surrounding the inner tubular structure and comprising a plurality of layers of a dielectric elastomeric material and a tubular elastic support structure, the elastic support structure configured to maintain a pre-stress in the dielectric elastomeric material layers,
  wherein the outer tubular structure is configured to contract in a radial direction around the inner tubular structure upon application of an actuation voltage signal across the dielectric elastomeric material layers.

The inner tubular structure defines an inner fluid flow path through the actuator, the inner fluid flow path being constricted upon application of the actuation voltage signal.

The tubular elastic support structure may comprise a plurality of layers alternating with one or more of the plurality of layers of the dielectric elastomeric material, or may alternatively comprise a single layer of the elastic support structure and a plurality of layers of the dielectric elastomeric material. The elastic support structure may be disposed around, beneath or interspersed between the plurality of layers of the dielectric elastomeric material.

The plurality of layers of the dielectric elastomeric material preferably alternate with interleaved electrode layers configured for applying the actuation voltage signal in parallel across the dielectric elastomeric material layers.

The tubular elastic support structure may comprise an auxetic structure configured such that a ratio between expansion in the circumferential direction and contraction in the axial direction of the tubular elastic support structure when unconstrained is zero or negative.

The inner tubular structure may be a braided tubular structure.

The actuator may be configured as a valveless actuator for a variable aortic tension device, where the actuator is configured to replace a resected portion of a blood vessel such as an aorta to allow for bi-directional blood flow during operation.

In an exemplary embodiment there is provided an implantable device comprising the actuator according to the above first aspect and an electronic controller configured to apply the actuation voltage signal to the dielectric elastomeric material layers. The device may be a cardiac assist device for attachment to an aorta of a patient, i.e. an intra-aortic pump, also termed a variable aortic tension device. In alternative embodiments the actuator may be an artificial sphincter, which may be used for example as a partial or complete replacement for a sphincter in the gastrointestinal tract, cardia, urethra, anus or another part of the body where toroidal constrictive muscle is required. The artificial sphincter may be configured such that the actuator is able to provide a peristaltic actuation, for example by having subdivided electrodes to enable different portions along the length of the actuator to be activated in sequence or by having a plurality of independently operable actuators in series.

The actuator may comprise electromagnetic shielding layers on inner and outer sides of the plurality of layers of the dielectric elastomeric material. The inner tubular structure may comprise the inner electromagnetic shielding layer, for example in the form of a braided tubular structure comprising an electrically conductive material.

In accordance with a second aspect of the invention there is provided a method of fabricating an actuator according to the first aspect, the method comprising the steps of:
  i) applying a layer of a dielectric elastomeric material to a substrate;
  ii) stretching the layer of dielectric elastomeric material to apply a pre-stress;
  iii) applying an electrode layer to a surface of the layer of dielectric elastomeric material;
  iv) applying a layer of an elastic support structure over the layer of dielectric elastomeric material while the layer is stretched; and
  v) relaxing the layer of dielectric elastomeric material and elastic support structure.

The layer of dielectric elastomeric material may be a seamless tubular layer applied around an outer surface of the substrate.

The elastic support structure applied over the layer of dielectric elastomeric material is preferably incompressible.

The method may further comprise a step of measuring an outer shape of the stretched layer of dielectric elastomeric material before the step of applying the electrode layer and using the measured shape to direct application of the electrode and elastic support structure layers. The outer shape may be measured by a non-contact measuring method such as by laser displacement measurement.

Steps i) to iii) may be repeated to build up a plurality of layers of the dielectric elastomeric material prior to applying the elastic support structure, with the method further comprising relaxing a current layer of dielectric elastomeric material to remove the pre-stress before applying a subsequent layer.

Steps i) to v) may be repeated to build up an actuator structure comprising layers of the elastic support structure alternating with one or more layers of the dielectric elastomeric material and associated electrodes.

The layers may be applied over an expandable substrate, expansion of the substrate providing the pre-stress to each layer of dielectric elastomeric material. The layers may for example be stretched by inflating the expandable substrate, which may be in the form of a balloon.

The layers of dielectric elastomeric material may be applied by a spray deposition process.

The elastic support structure may be applied by a three dimensional printing process, for example via extrusion or paste deposition.

DETAILED DESCRIPTION

The invention is described in further detail below by way of example and with reference to the accompanying drawings, in which:

FIG. 2b is a schematic diagram illustrating the arrangements of interleaving electrodes for the exemplary actuator of FIG. 2a;

Figure 1A:
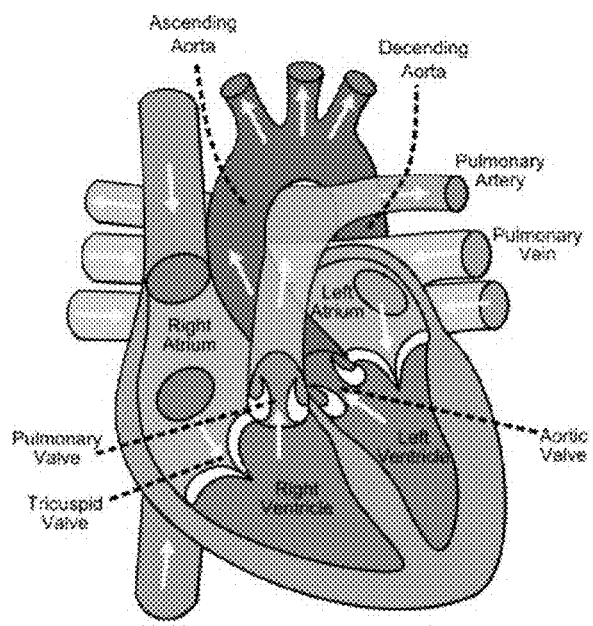
FIG. 1a is a schematic cutaway diagram illustrating the main components of a human heart.
Figure 1B:
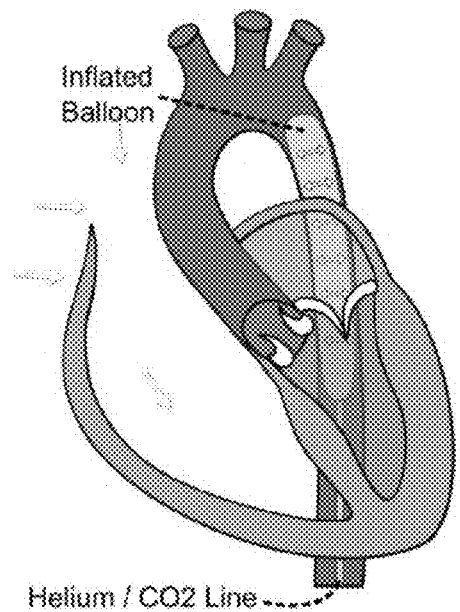
FIG. 1b is a schematic illustration of an intra-aortic balloon pump in place within an aorta.
Figure 1C:
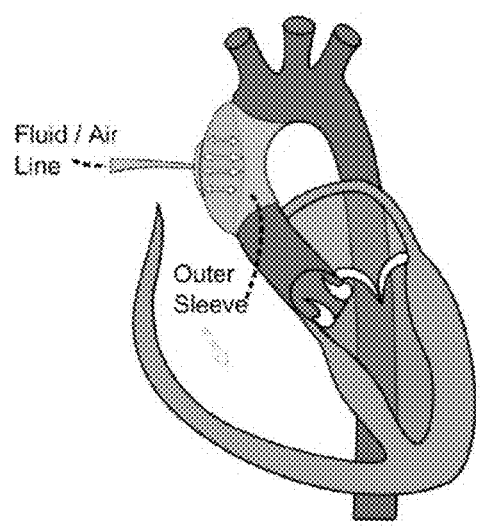
FIG. 1c is a schematic illustration of an extra-aortic balloon pump in place around an aorta.

Embodiments of the invention have certain similarities to existing Extra Aortic Balloon Pump devices. However, instead of using inflatable balloons, the invention employs layers of a dielectric elastomeric material to provide a pumping action in place of pneumatically inflating bags or hydraulic sleeves.

Dielectric elastomers (DEs) are electroactive materials that convert electrical energy to or from mechanical energy. The essential property of such materials is their ability to transmit electrostatic forces without conduction (thus making them insulators). Actuation of a dielectric elastomeric actuator (DEA) system is achieved through the introduction of compliant (stretchable) electrodes on either side of a suitably chosen elastomer.

Suitability is based on the criteria of high dielectric breakdown constant, low modulus, high relative permittivity and low viscosity (Nguyen et al, 2009). Exemplary dielectric elastomer materials may be based around silicone or acrylic elastomers, particular examples being viscoelastic foamed acrylic elastomer tapes such as VHB acrylic tapes, available from 3M, or low hardness, high elongation Silicone such as TC-5005 A/B-C.

The combination of electrical insulation and elasticity allows for active control of the dimensions of an elastomer film by exploiting both the attraction between opposite charges on opposing film surfaces and the repulsion between like charges on the same film surface. Compliant electrodes on the surfaces of the film hold these charges without impeding the film's deformation (Capri et al, 2003). The forces that generate the actuation come from electrostrictive attraction (Coulombs Force) between the two electrodes, though this can often be modeled as being caused by Maxwell Pressure (Kofod, 2001).

DEAs have been selected as the most suitable Electro Active Polymer (EAP) actuator for the invention, due to the high stress, realisable force and the near instantaneous response times attainable. They are the only known class of EAP that can match or exceed natural muscle in all major metrics (Madden et al, 2008).

DEAs can potentially address a number of problematic issues with current ventricular assist devices. The first is the creation of a fully in vivo device. There presently exists no commercial implantable VAD, which does not depend on some form of percutaneous tubing or wiring. The invention of such a system would grant the patient mobility, and freedom from full time hospital care. While there are a small number of US patents existing for theoretical devices which claim to be fully implantable (such as U.S. Pat. No. 4,925,443 or U.S. Pat. No. 7,198,594), these systems are fully mechanical and contain many rigid linkages and hinges. It is uncertain how such devices would receive enough power to consistently actuate the mechanical linkages for a prolonged period of time using a relatively low capacity pacemaker style battery. By contrast, an actuator according to the invention, through using electroactive polymeric actuation, is expected to have a typical power consumption in the sub 1 Watt category (Carpi et al 2008). These actuators are in effect compliant capacitors, and as such the power supplied for actuation is held as an electric charge. This charge can be partially recouped back into the system at the end of each actuation cycle, thus increasing power efficiency.

An implantable device according to an embodiment of the invention will preferably have an absolute minimum of exposed non-biological materials, the only exposed sections preferably being an outer biocompatible coating and an inner tube blood flow path. The outer biocompatible coating may for example be composed of a silicone or a parylene (poly(p-xylylene)) material. The inner tube structure may be in the form of an aortic graft weave, which promotes cellular growth on its surface. The inner tubular structure is preferably woven to form a collapsible structure, for example using origami-type techniques (Guest & Pellegrino, 1994) which allow the core to radially shrink with the contractive force from the biaxial braid without kinking or fatiguing.

A device according to a preferred embodiment of the invention may consist of an entirely compliant structure, i.e. without the presence of any rigid bodies other than at most two anchor point rings at either end of the device for enabling attachment of the device to a blood vessel such as the aorta. Such a structure would greatly enhance implantability, allowing the entire device to be embedded inside the pericardium.

Devices according to embodiments of the invention are envisaged to be made using a customisable manufacturing technique for creating a fully compliant structure with a low cross-sectional profile that is capable of fitting in place of the lower ascending aorta, which is where the pumping effect is recognised as being optimised (Furman et al, 1971). By using a bespoke technique for manufacturing, each device can be individually sized and fitted according to the patient's measurements, which may for example be obtained from C/T or MRI scan data. Such a fabrication method is envisaged to be achievable by using combinations of 3D printing, direct write assembly and multi-axis spray deposition. Doing so will greatly enhance the effectiveness of the device by ensuring that the individual requirements of each patient is met at the device manufacturing stage.

An exemplary pump is envisaged to comprise six main parts:
1) An inner tube consisting of a biocompatible 'Gelweave'-like Aorta graft (Gelweave is a tradename for implantable aortic graft materials, available from Vascutek, part of the Terumo Group of companies).
2) A bi-axial or tri-axial woven inner tubular support structure that decreases in diameter at a rate of at least 1:1 per longitudinal extension.
3) A multi-layer Dielectric Elastomer Actuator (DEA) with each layer being prestretched before being patterned with a conformal and compliant electrode.
4) An auxetic patterned support structure, extruded onto the stretched DEA layer. This would be made from an essentially incompressible yet flexible high durometer elastomer (having a high Shore A or low Shore D hardness, for example between 80 and 100 Shore A or between 45 and 55 Shore D). This will act as a compressive support structure to hold the tensioned actuator, keeping the system in a state of 'tensegrity'. This could be described as a Minimum Energy Structure.
5) An outer insulator, to shield the electrical aspects of the actuator from the patient's heart and other organs.

An additional layer, which may also be auxetic (for example in the form of a foam-like material), may be provided between the woven inner tubular support structure and DEA to mechanically couple and electrically insulate the outer actuator layer and the inner axial weave.

The term 'auxetic' describes a material with an effective negative Poisson ratio, i.e. where expansion in one direction results in expansion (or no contraction) in another orthogonal direction. An auxetic material in the form of a tubular structure may therefore expand in a longitudinal direction and either remain unchanged in diameter or increase in diameter, as opposed to a non-auxetic material where the diameter will decrease.

The term 'tensegrity' relates to a compliant and balanced system comprising hardened, or incompressible but flexible, skeletal elements under compression, which serve to hold elastic elements under tension.

In relation to the DEA component of the device, the elastomer membrane, electrode and support structure may be fabricated according to the following techniques.

1) Membrane. This is to be a tubular device, with reliability as its most important aspect. To achieve a balance between reliability and exertable force, it is proposed to spray deposit multiple layers of a bio-compatible solvent reduced elastomer such as a silicone in a seamless manner around a tubular inner support structure. The efficiency and force output of a DEA depends on having as thin a cross sectional membrane as is possible (ideally 10-50 µm). This allows for the Maxwell Forces between interspersed electrodes layers to attain a maximum attractive force per unit charge. (Carpi et al 2008). A currently preferred technique to achieve this is to atomise and spray each layer with a solvent diluted elastomer, for example as disclosed in Araomi et al. (2011). To increase the electrical efficiency of the overall system, a high dielectric constant ceramic filler may be integrated into the matrix.

2) Electrode. The electrodes must be capable of isotropic expansion (of at least 50% in this case) without significant loss of conductivity. The material should also preferably be fully bio-compatible, although since the electrodes should be entirely encapsulated this may not be an essential requirement. The requirement for biocompatibility may rule out a number of commonly used DEA carbon based materials. Alternative materials may be formed from embedding noble metals such as platinum salts into an un-vulcanised elastomer matrix. When these are reduced, the salts form conductive platinum 'nodules' which are embedded into the surface of the polymer, for example as disclosed in Delille et al (2009). These nodules would need to be interconnected with a high conductivity layer, which may for example comprise a carbon nanotube or reduced graphene oxide (RGO) ink, or an ionic hydrogel, as for example described by Keplinger et al in "Stretchable, transparent, ionic conductors", Science 341(6149): 984-987. Such materials would allow the electrode to be self-clearing (which increases reliability), while retaining conductivity over a high mechanical strain (see for example Yuan et al. 2009). There would also be advantages to efficiency by increasing the charge carrying capacity of each layer.

3) Support Structure. The fabrication of a DEA actuator requires the introduction of 'pre-stretch' to the elastic membrane. This pre-strain provides mechanical amplification and increases dielectric strength (Capri et al. 2008). Pre-strains are often large (>100%), and achieving this requires high stresses (typically in the MPa range). Holding this prestretch from collapsing back on itself, whilst still retaining a fully compliant 'muscle' structure is challenging. Most researchers use rigid plastic rings or springs for test purposes, but such systems are not viable for an in vivo device. There are a small number of research groups examining the use of flexible support structures to partially hold a prestretch, while partially contracting to out-of-plane 3D forms. Kofod et al (2006) deem such buckled systems to be Minimum-Energy Structures at the point that they reach a final resting conformation. Preferred embodiments of the invention envisage the use of auxetic layers, such as auxetic chiral honeycomb structures, to hold this stretch without causing an out-of-plane buckling. Such auxetic layers may be applied using 3D printing techniques.

Preferred embodiments of the invention are proposed to form a fully implanted counter-pulsation device. The form of such a device 10 connected to an aorta 11 is shown schematically in partial cutaway form in FIG. 1d. Electrical connections to a control unit are not shown. Unlike currently available devices that rely on pneumatically driven balloons to create the counter-pressure in the aorta, devices according to preferred embodiments of the invention using DEAs are expected to have a low power consumption, thereby allowing them to run off an implanted battery or via transcutaneous inductive power transfer, having effectively silent operation, a high speed of actuation, high strain, and potentially higher force output than natural muscle.

The exemplary fluid pump device 10 comprises a number of layers, each preferably seamlessly fabricated over a previous layer. The innermost layer (not shown in FIG. 1d) is preferably a biocompatible layer defining an inner blood flow path, which may for example be made of a tube woven from a waterproof gelatin-sealed polyester. The woven tube may for example be similar in concept to commercially available grafts such as Vascutek Gelweave structures but may differ in weave structure due to the requirement for a collapsible circumference to prevent kinks, tears and fatiguing. Surrounding the blood path is a bi-axially braided flexible support structure 12, which acts both as a support for the surrounding DEA and as a mechanical linkage for conversion of the longitudinal expansion to circumferential contraction. The DEA 13 connected to and surrounding the support structure 12 comprises a plurality of layers of a dielectric elastomeric material and associated compliant electrode layers. An outer support structure 14 is provided around the outside of the elastomeric actuator. This support structure 14 is required to hold the pre-strain tension which is added to the actuator membranes, both for mechanical amplification and to improve dielectric properties. A further outer layer may be provided around the support structure 14 to provide a biocompatible layer protecting the inner components.

Figure 1D:
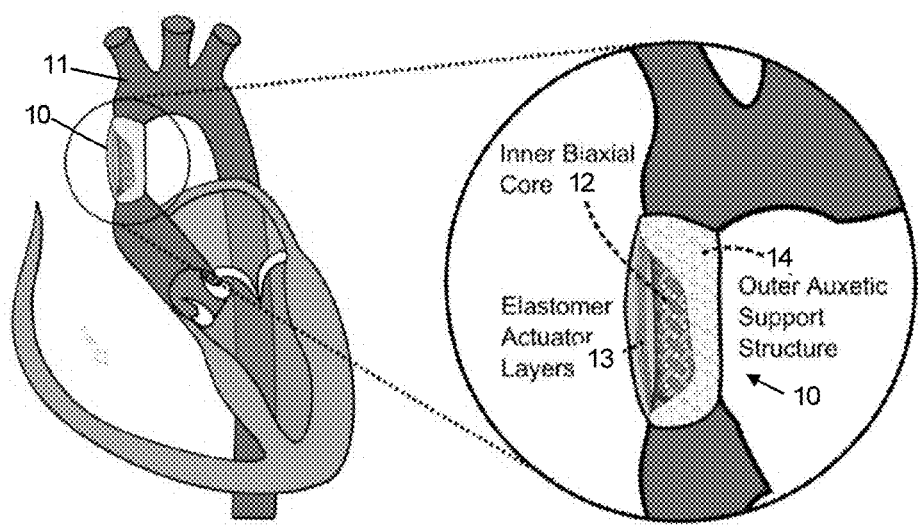
FIG. 1d is a schematic drawing of an exemplary actuator connected to an aorta.
Figure 2A:
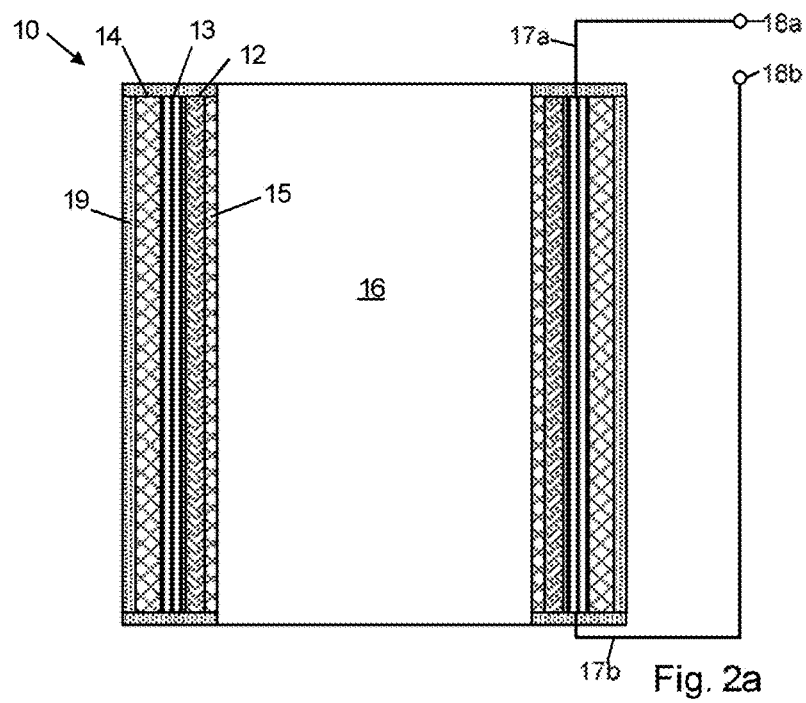
FIG. 2a is a schematic cross section of the structure of an exemplary actuator.

FIG. 2a illustrates a schematic cross-sectional view of an exemplary fluid pump actuator device 10 of the type shown in FIG. 1d. The device 10 comprises an inner biocompatible layer 15 defining an inner fluid flow path 16, around which is provided the flexible support structure 12, which is preferably in the form of a tubular braid. Surrounding the support structure 12 is the dielectric elastomeric actuator structure 13. Electrical connections 17a, 17b are provided for applying an electrical signal via terminals 18a, 18b to the actuator structure 13. An outer support structure 14 surrounds the actuator structure 13, which maintains a pre-strain in the layers of the actuator structure 13. In the embodiment shown, the outer support structure 14 is a separate layer surrounding the actuator structure. In alternative embodiments at least some of the outer support structure may be incorporated into the actuator structure, for example by alternating one or more of the plurality of layers of dielectric elastomeric material with a layer of the support structure. A further biocompatible outer layer 19 may also be provided that surrounds the outer support structure 14, which may also extend over the ends of the device 10 to further protect the various inner structures.

Figure 2B:
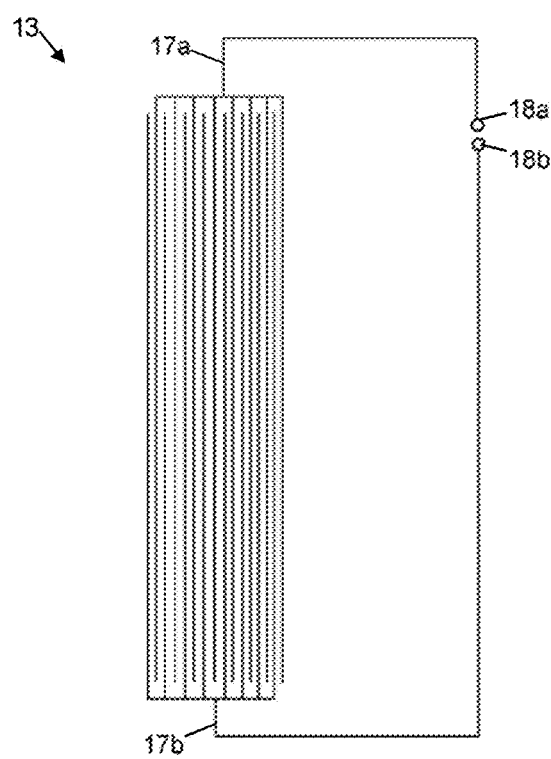

To allow each layer of the actuator structure to be operated in parallel, and to minimise the voltage required, the electrodes are preferably arranged in an interleaved structure as illustrated schematically in FIG. 2b. Electrical connections to the actuator structure 13 can then be readily made at opposing ends of the device. In operation, applying a voltage to actuator structure 13 via electrical connections 17a, 17b causes the actuator device 10 to contract in a radial direction, thereby constricting the inner fluid flow path 16. Removal of the voltage causes the device 10 to expand by returning to its relaxed form.

Figure 3:
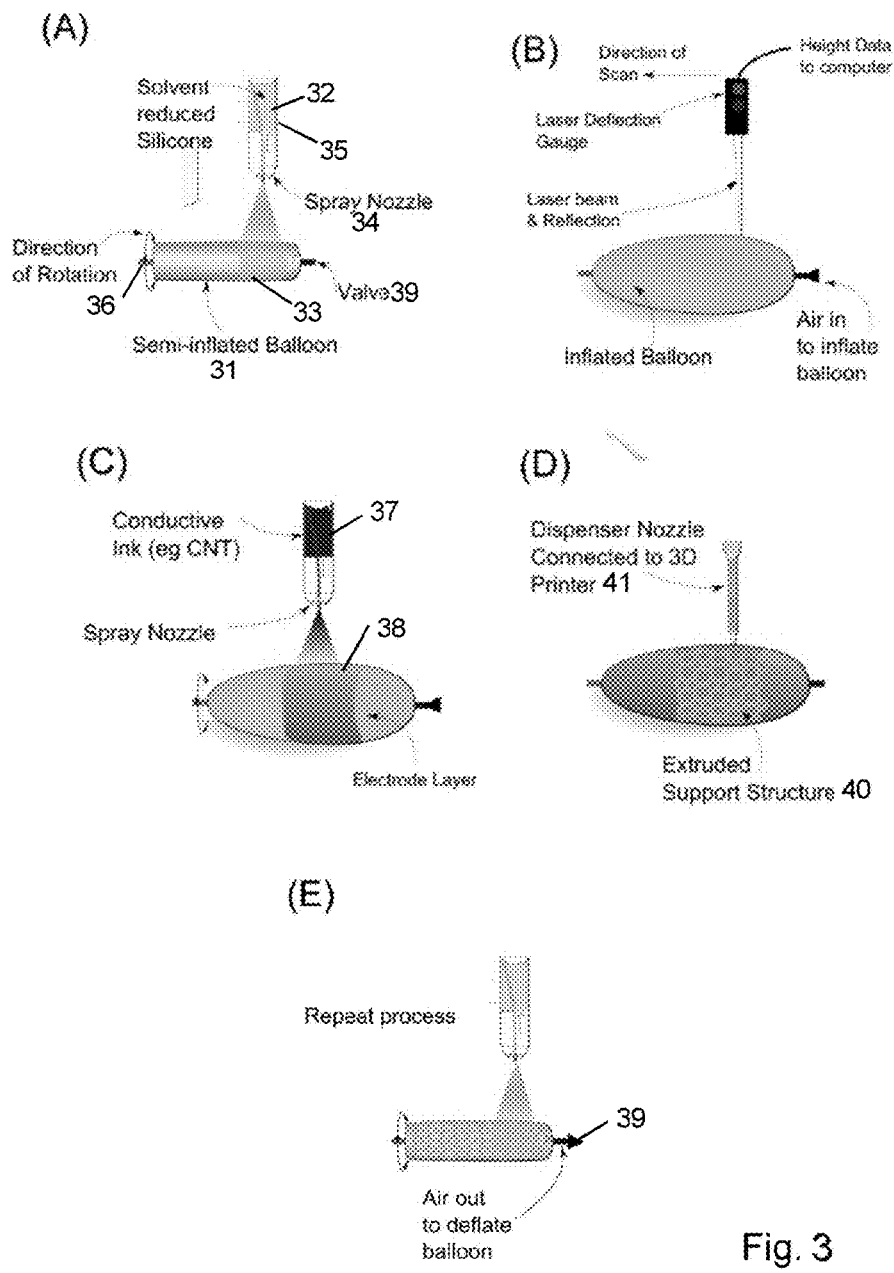
FIG. 3 is a series of schematic illustrations showing an exemplary process for fabricating the elastomeric and support structure layers of an actuator.

FIG. 3 illustrates schematically an exemplary process for fabricating the electroactive structure and associated support structure for a fluid pump actuator. In a first step (A), a semi-inflated balloon 31 is spray-coated with a solution 32 of an elastomer in a suitable solvent, using a spray nozzle 34 connected to a reservoir 35 containing the solvent-reduced elastomer 32. As the balloon 31 rotates about its longitudinal axis 36, a thin uniform layer 33 of elastomer is deposited on the outer surface of the balloon 31. In a second step (B), after the solvent is removed and the elastomer has vulcanised, the balloon 31 is further inflated through a valve 39 to stretch the elastomer layer 33. Since the balloon may not inflate uniformly along its length, as an optional further step a scan may be made of the surface of the inflated balloon to establish its non-uniformity. This will ensure the print-head sprays each subsequent electrode layer or deposits subsequent support layers from a constant height above the balloon. To achieve this scan, a laser displacement sensor may be used to acquire data corresponding to height of the balloon along its axis of rotation. As the membrane is symmetric around this axis, the height data can be digitally/virtually rotated within a CAD package, resulting in an overall 3 dimensional structure. This virtual 3D structure mesh can then be used to generate computer numeric control code (gcode) for subsequent operations. In step (C), a conductive ink 37, which may for example be a dispersion of carbon nanotubes, is then applied, also by spray coating, forming a thin uniform conductive electrode 38 over the elastomeric layer 33. Applying the conductive layer after inflating the balloon and stretching the elastomeric layer 33 ensures that the electrode 38 will remain conductive in subsequent use, whereas if the conductive ink 37 is applied before inflation the electrode 38 may become discontinuous when the electroactive layer 33 is stretched.

Steps (A), (B) and (C) may be repeated as required to build up a multi-layer electroactive polymer structure, with interleaving electrodes applied between each layer to allow for parallel application of an actuation voltage across each of the layers.

In a fourth step (D), a tubular elastic support structure 40 is deposited over the layer (or layers) of dielectric elastomeric material. The support structure 40 may be applied from a computer-controlled dispensing nozzle, relative movement of the balloon 31 and the dispensing nozzle 41 allowing a desired pattern to be built up over the underlying elastomeric layer(s).

After the elastic support structure 40 is applied, the process A-D may be repeated, after deflating the balloon 31 by letting air out of the balloon 31 through the valve 39 (step (E)).

Alternative methods of applying the various layers of material for making up the fluid pump actuator structure may be used, for example by applying one or more of the layers around the balloon in a pre-fabricated form or by forming one or more of the layers in a planar form and then wrapping around a cylindrical former and securing in place.

Controlled additions of high dielectric constant fillers (such as ceramic particulates like alumina $Al_2O_3$ or titanium dioxide $TiO_2$) may be added to the elastomer to both increase the dielectric breakdown strength of the membrane, and decrease the activation voltage. This has been attempted by some research groups, via spin-coating (Carpi & Rossi, 2005). The results have been moderately successful, but issues relating to clumping of particulates have hindered progress. Atomising the rubber/ceramic compound and/or incorporating a chemical dispersant into the solvent, elastomer and particulate mixture would help to reduce these clumping issues.

The choice of base elastomer membrane is limited by factors of biocompatibility, durability and dielectric properties. There are a number of silicones (such as TC Enterprise 5005 A/B-C and Dow Corning HS3) which are generally recommended for their good performance and durability, and are therefore proposed as preferred materials for the elastomeric material. Polyurethane may alternatively be used, for example if the resilience of PDMS silicone is found to be unsatisfactory. The material used for the elastomer membrane should preferably be biocompatible, although this might not be a necessary requirement if the actuator structure is entirely encapsulated with a biocompatible material.

A fine mesh of support structure may be printed between every layer, or possibly may only be required every few layers deposited. The specifics of this compliant layer are discussed further below. This spraying process must be repeated a number of times to build up an actuator layer with enough generating force to displace the required 5 ml of blood per 'beat' for the fluid pump actuator to be used as part of a cardiac assist device.

In relation to the conductive inks, materials other than carbon-based dispersions may be used. One alternative is an elastomer impregnated with noble metal salts, such as Platinum $[Pt(NH_3)_4]Cl_2$ or Palladium $[Pd(NH_3)_4]Cl_2$. These salts can be reduced using a strong reducing agent such as lithium or sodium borohydride, a technique known for use in fabricating electrodes for ionic polymer metal composite actuators. Satisfactory experimental verification of this method has been completed by Urdaneta et al (2007). A second stretchable electrode layer, composed of single or multi wall carbon nano-tubes may also be applied (see for example Hu et al 2009), which will give the system greater charge carrying capacity on each electrode layer due to the metal nodules embedded in the membrane increasing surface area, but without sacrificing strain performance due to the compliant but lower conductivity nanotube layer.

Alternative electrode compositions may involve deposition of graphene or reduced graphene oxide (RGO) dispersions delivered for example using ink-jetting techniques, or powder blasted graphite/elastomer composite electrodes commonly used currently in research.

As previously discussed, a completed cardiac assist device preferably consists of a woven internal aortic graft surrounded by stretched actuator layers. The process of installing the device will involve the surgeon removing a section of the natural ascending aorta and inserting the artificial graft in its place. This requires invasive surgery, but it is not an unusual procedure to replace a piece of diseased aorta. It affords many advantages, the most significant of which is a re-introduction of elastic compliancy in the aorta itself. Due to ageing or disease the inner layer of the aorta (Tunica Intima) will begin to develop stenosis (or narrowing of bore) and loss of elasticity. This becomes problematic as the heart contracts and forces blood through the open aortic valve. The walls of the artery must be flexible enough to absorb the force as blood surges into it, and then return to its relaxed state as the force subsides. It also must have a large enough diameter to not stress the heart by requiring high pressure to get the correct volume of blood through a narrow artery. By replacing a section of the ascending aorta, the work required both by the dielectric actuator layer and by the heart itself is expected to be greatly decreased, and is also expected to allow the device to be more resilient to failure by removing any seams or discontinuities.

The innermost layer of an exemplary cardiac assist device comprising a fluid pump actuator according to the invention will need to be a watertight collapsible structure, having properties similar to commercially available bio-promoting woven aorta grafts. The main difference from these devices is the requirement for the graft to be collapsible around its circumference without kinking, tearing or wearing out over many millions of actuations. This is proposed to be achieved using auxetic textiles.

Figure 4:
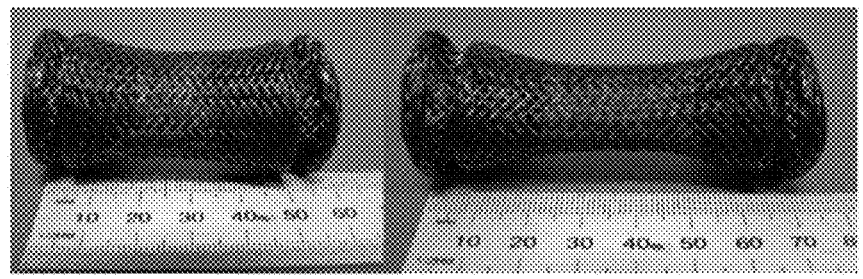
FIGS. 4a and 4b are photographs of exemplary braided tubular structures for an inner support structure of an actuator, in relaxed and extended forms.

The surrounding mechanical support for the stretched actuator will be integrated with the woven layer. As previously explained, a DEA expands isotropically when electrically stimulated. For a planar material form, expansion within the XY plane creates a reduction in thickness along the Z axis. This produces an inverted or 'anti-muscle' effect. To create a circumferential reduction within the inner tube graft resulting from this longitudinal expansion, some form of mechanical means must be employed. It is proposed to use a biaxial or triaxial woven structure to create this mechanical conversion. FIG. 4 shows a simple biaxial braid (Hercules weave), created from monofilament, which exhibits the type of behaviour required. It can be seen in FIG. 4 that this type of braid shows a reduction in diameter of around 1.1 of a longitudinal extension, i.e. if the length extends by 100% the diameter reduces by 55%.

The fail-safe aspect of the geometry makes a cardiac assist device according to the invention a particularly suitable solution. The braid is surrounded by a stretched elastic membrane (the DEA), which has the effect of pulling the structure into open (i.e. non-constricted) form when it is not energised. Should the active elements of the device fail while in use, the natural position for the graft to settle would be the inactive-open form, thereby not restricting blood flow through the aorta.

Figure 5:
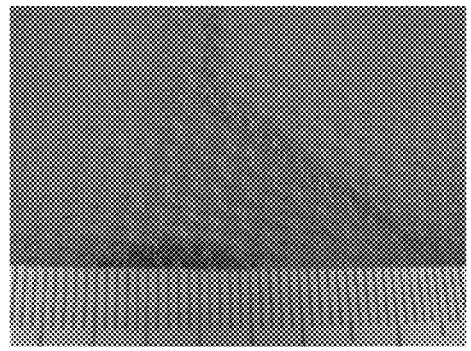
FIG. 5 is a photograph of an exemplary auxetic structure formed from UV cured acrylic resin on a stretched acrylic elastomer layer.

An example of an auxetic structure, made using UV cured acrylic ink patterned on to a stretched acrylic elastomer, is shown in FIG. 5. The scale bar is in millimeters. This structure is a variation on the types of structures disclosed in Alderson et al (2010).

The braided tubular structure may for example be constructed out of an electrically conductive material so as to create a Faraday cage, which would result in blocking of electromagnetic radiation.

The outer support structure and covering of the proposed device is analogous in function to the outer membrane of the aorta (tunica adventitia). This membrane is composed predominantly of collagen fibres, with some elastic fibres present. The collagen in the adventitia prevents the elastic arteries from stretching beyond their physiological limits during systole. Alongside this outer-limiting function, the proposed device will require support to prevent it collapsing in on itself due to the pre-strained elastic membranes. In effect, what is desired is a system held in a state of "tensegrity"—i.e. tensional integrity or floating compression. When a stretched elastomer is laminated to a flat inextensible but pliant planar frame, a complex shape is formed through the transfer of elastic energy from the film to the frame. Kofod et al (2006) deemed this buckled system to be a minimum-energy structure (MES) when it reaches a final resting conformation. A shift in the minimum energy state can be achieved by either adding or removing elastic energy from the system. Energy is initially added to the system by introducing 'pre-stretch' to the elastic film, and then coupled with the inextensible frame while under strain. The use of such support frames allows flexibility while holding a level of pre-stretch, which is desirable. Unfortunately the systems have a tendency to form complex 3D shapes, which are difficult to control. To achieve a MES form it is proposed instead to use a system whereby a flexible but high durometer (hardness) elastomer is applied, for example by extrusion, directly onto the stretched membrane balloons, using direct write assembly 3D printing techniques. This hard elastomer can contain additives such as nano-cellulose or mineral fillers such as alumina or kaolin to increase the compressive strength.

The geometrical form that the support matrix takes may be that of an auxetic chiral honeycomb, for example of a type disclosed by Alderson et al (2010). Considering the elastomer film as negligibly dimensioned in thickness and prestretched in all directions equally, then its actuation alone could be considered as auxetic (having a negative Poisson ratio)—i.e. having uniaxial elongation. The hypothesis here is a structure that shows the same elongation tendencies would be better for building a compressive support matrix.

Abramovitch et al (2010) discussed the failure modes and load carrying ability of chiral honeycomb structures that provide the possibility to partially decouple failure loads in out of plane shear and compression. This is due to the cylindrical shape providing enhanced compressive strength, while the ligaments resist shear, enabling a honeycomb with resonant properties to be tailored to a specific application.

An important and common feature of many auxetic honeycombs is they have been shown to give synclastic curvature, i.e. they form domes rather than saddle structures when bent out of plane. When creating tubular or toroidal muscles, this is a very desirable property.

The honeycomb examples in Alderson et al (2010) are only a small selection of the various geometries that may be used to make up an auxetic matrix. Specific design and tailoring of mechanical responses may be done using computer modelling, and the geometry of a particular structure may thereby be refined over simulation iterations in order to find the most suitable mechanical response.

Applying the elastomeric layers on an inflated balloon may result in a non-uniform, non-planar shape which may make printing of any support structure more complicated, To achieve uniform printing on complex forms, a high accuracy extrusion pump (such as a nScrypt SmartPump) may be used on a modified 5 Axis CNC router, a custom Cartesian robot or a delta robot gantry which is provided with data describing the surface of the inflated balloon.

Electrical control circuitry is required to drive the fluid pump actuator. For a cardiac assist device this circuitry will consist primarily of an implanted electrocardiogram (ECG) to monitor the heartbeat via a high-speed microcontroller, a proportional DC-DC voltage transformer to energise the DEA, and a transcutaneously rechargeable (inductive) battery. These are all well-developed technologies used in many other implantable devices. For closed-loop control the device may incorporate a sensor so that the position of the actuator is known at any one time. There are a number of published methods for doing this, either with a separate passive DEA membrane configured in sensor mode, or using a method known as 'self-sensing capability', which measures the impedance of the active multi-layer actuator. (Chuc et al. 2008). This will enable fine grained control, for the creation of desired pressure notches (for example, mimicking the dicrotic notch of a normal healthy heart coinciding with closure of the aortic valve).

Without further modification, an electromagnetic radiation field produced by the device may be produced that is greater than desired or may exceed regulatory limits. According to a study conducted by McKenzie et al (2008), the static electric fields of an idealised DEA can be kept within the acceptable limits of the IEEE Standard C95.6-2002. Currently there are no specific recommendations for long term exposure, though the IEEE propose that it should be in the same order as short term. The main requirement to reduce emitted radiation is to keep the elastic membranes as thin as possible, thus reducing the required activation voltage. Also, the design should ensure an even number of layers which reduces the fringe field strength by orders of magnitude.

Introducing ceramic particulates into the membrane may further reduce electromagnetic radiation, thus reducing the required electric activation per output force. Also, the actuator membrane layer of the device may be encapsulated on both outer and inner surfaces with appropriate EMR shielding. This may be at least partially provided by using the Faraday cage effects of a biaxial braid woven using conductive material. External shielding may be provided by the outer support structures and a device encapsulation layer.

A possible risk is in the potential breakdown and tearing of the elastomer layers. It has already been found experimentally that the use of tessellated support structures such as auxetic honeycombs can act as a 'rip-stop' to the membrane. Even if a tear should appear, the effect should therefore be limited to only a small area of one layer. The use of such auxetic materials may therefore also be beneficial in providing a more resilient and long-lasting device.

Figure 6:
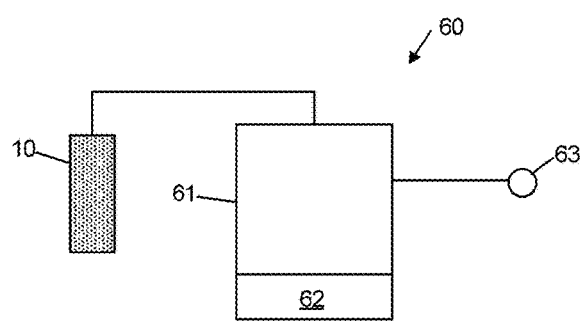
FIG. 6 is a schematic diagram of a cardiac assist device incorporating an actuator.

FIG. 6 illustrates schematically a cardiac assist device 60 incorporating a fluid pump actuator 10 of the type described herein. The device 60 further comprises electronic control circuitry 61, and incorporates a battery 62. The control circuitry is preferably configured such that the battery 62 is chargeable via a transdermal connection, for example by an inductive link with an external charger. An electrocardiogram sensor 63 is preferably provided to enable the circuitry 61 to synchronise pumping action of the fluid pump 10 with the natural heartbeat of the patient. Further components may also be incorporated, such as a sensor to determine the position of the actuator 10 for closed loop control, as described above.

Figure 7:
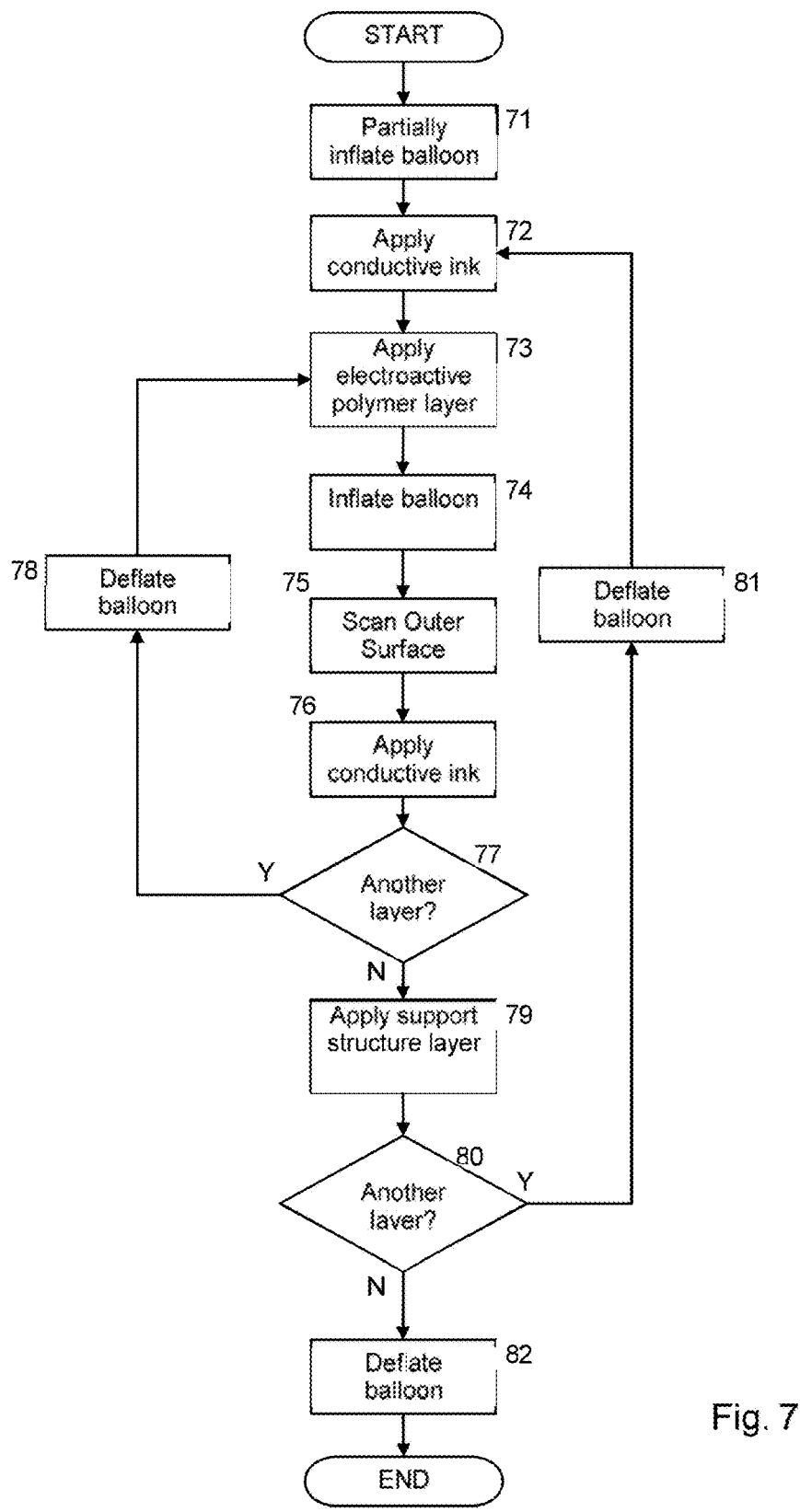
FIG. 7 is a schematic flow diagram of an exemplary method of forming the electroactive and support structure layers of an exemplary actuator.

FIG. 7 illustrates schematically a method for fabricating the electroactive and support structure layers of a fluid pump actuator according to an embodiment of the invention, the method corresponding with the process illustrated in FIG. 3 and described above. The method starts (step 71) by partially inflating a balloon around which the structures are to be deposited. The balloon may form a part of the final device once fabricated, or may be removed after the fabrication process is complete. A first layer of conductive ink is deposited on the surface of the balloon (step 72). The conductive ink may alternatively be deposited after first inflating the balloon, to ensure continuity of the electrode layer deposited, followed by deflation before the next step. A layer of electroactive polymer material is then applied (step 73), following which, after the layer is set, the balloon is inflated (step 74). A further layer of conductive ink is then applied over the electroactive material layer (step 76), optionally after scanning the surface of the inflated balloon to determine its shape (step 75, described above in relation to FIG. 3). If a further layer is required (step 77), the balloon is deflated (step 78) and the process is then repeated. Once a required number of successive electroactive layers have been deposited, a support structure layer is deposited (step 79). The whole process may then be repeated again, if further layers of electroactive material and support structure layers are required (step 80), after deflating the balloon again (step 81). Finally, once all layers have been applied the balloon is deflated (step 82) and the process finishes.

Other embodiments are intentionally within the scope of the invention as defined by the appended claims.

REFERENCES

Abramovitch H, Burgard M., Edery-Azulay L, Evans K. E., Hoffmeister M., Miller W., Scarpa F., Smith C. W., Tee K. F., (2010) Smart tetrachiral and hexachiral honeycomb: Sensing and impact detection. Composites Science and Technology Volume 70, Issue 7, July 2010, Pages 1072-1079

Alderson A, Alderson K. L., Attard D., Evans K. E., Gatt R., Grima J. N., Miller W., Ravirala N., Smith C. W., Zied K. (2010) Elastic constants of 3-, 4- and 6-connected chiral and anti-chiral honeycombs subject to uniaxial in-plane loading. Composites Science and Technology 70 (2010) 1042-1048

Araomi O. A., Conn A. T., Ling C. S, Rossiter J. M., Vaidyanthan R, Burgess S. C. (2011) Spray deposited multilayer dielectric elastomer actuators. Sensors and Actuators A: Physical, Volume 167, Issue 2, June 2011, Pages 459-467

Barnard S P, Hasan A, Forty J, Hilton C J, Dark J H. (1995) Mechanical ventricular assistance for the failing right ventricle after cardiac transplantation. Eur. J. Cardiothorac., 9 (6), 297.

Carpi, F., Rossi, D. D., (2005), Improvement of electromechanical actuating performances of a silicone dielectric elastomer by dispersion of titanium dioxide powder, Dielectrics and Electrical Insulation, IEEE Transactions on, vol. 12, no. 4, pp. 835-843, August 2005.

Carpi F, Chiarelli P, Mazzoldi A, De Rossi D (2003) "Electromechanical characterisation of dielectric elastomer planar actuators: comparative evaluation of different electrode materials and different counterloads" Sensors and Actuators A 107 85-95

Carpi, De Rossi, Kornbluh, Pelrine & Sommer-Larsen editors. (2008) "Electromechanical Transduction effects in dielectric elastomers: Actuation, Sensing, Stiffness Modulation and Electric Energy Generation." Chapter 1 (Springer, 2008)

Chuc N. H, Thuy D. V, Park J., KimD., Koo, J, Lee Y., Nam J. D., Choi H. R. (2008) A dielectric elastomer actuator with self-sensing capability. EAPAD (2008) Proc of SPIE Vol 6927, 69252A.

Dedhia J. D, Kotemane N. C., Ahmed A. B., (2008) Intra Aortic Balloon Pump (IABP): Past, Present and Future. Indian Journal of Anaesthesia 2008; 52 (4):387-396.

Delille R, Urdaneta M, Hsieh K, Smela E. (2009) Compliant electrodes based on platinum salt reduction in a urethane matrix. Smart Materials and Structures 16 S272-S279).

Furman S, Attai L, Parker B. Cardiac support by periaortic diastolic augmentation. NY State J Medicine. 1970; 70: 1964-1969.

Furman S, Whitman R, Stewart J, Parker B, McMullen M. Proximity to aortic valve and unidirectionality as prime factors in counterpulsation effectiveness. Trans Am Soc Artif Int Organs. 1971; 17: 153-159.

Ganau A, Devereux R B, Pickering T G, Roman M J, Schnall P L, Santucci S, Spitzer M C, Laragh J H. (1990). Relation of left ventricular hemodynamic load and contractile performance to left ventricular mass in hypertension. Circulation, 81 (1), 25-36.

Guest, S. D & Pellegrino, S., (1994) The folding of triangulated Cylinder, Part I, Geometric considerations, J. of Appl. Mech. 61, 773-777 (1994)

Glazzard M., and Breedon P, (2013), Weft-knitted auxetic textile design, Status Solidi Journal (accepted subject to revisions).

Hu, L, Yuan, Wei, B., Gruner, P. Pei G, (2009) Highly stretchable, conductive, and transparent nanotube thin films, Applied Physics Letters, vol. 94, no. 16, pp. 161108-161108-3, April 2009.

Keplinger et al., Stretchable, transparent, ionic conductors, Science 341(6149): 984-987.

Kofod, G. Paajanen M, Bauer S (2006) Self-organized minimum-energy structures for dielectric elastomer actuators (2006) Appl Phys A 85, 141-143.

Kofod G. (2001) "Dielectric Elastomer Actuators" PhD Thesis—The Technical University of Denmark Legget, M. E. William S. Peters, W. S., Milsom F. P., Clark, J. S., West, T. M, French, R. L. and Merry, A. F. (2005). Extra-Aortic Balloon Counterpulsation: An Intraoperative Feasibility Study. Circulation. 2005 Aug. 30; 112(9 Suppl):I26-31.

Madden J. D. W. (2008) Dielectric elastomers as high performance electroactive polymers. In Fedrico Carpi, Danilo De Rossi, Roy Kornbluh, Ronald Perline, and Peter Sommer-Larson, editors, Dielectric Elastomers as Electromechanical Transducers, chapter 2. Elsevier, 2008.

McKenzie A. C., Calius E. P., Anderson I. A. (2008) Electric field around a dielectric elastomer actuator in proximity to the human body. EAPAD (2008) Proc of SPIE Vol 6927, 69252A.

Mulgaonkar A., Kornbluh R., Herr H. (2008) A New Frontier for Orthotics and Prosthetics: Application of Dielectric Elastomer Actuators to Bionics, Dielectric Elastomers as Electromechanical Transducers: Fundamentals, Materials, Devices, Models & Applications of an Emerging Electroactive Polymer Technology. Elsevier; 2008.

Nguyen H C, Doan V T, Park J, Koo J C, Lee Y, Nam J D and Choi H R. (2009) "The effects of additives on the actuating performances of a dielectric elastomer actuator" Smart Mater. Struct. 18

Raman, J., Loor G., London M., Jolly N., (2010) Subclavian Artery Access for Ambulatory Balloon Pump Insertion. Ann Thorac Surg. 2010 September; 90(3):1032-4. doi: 10.1016.

Song, Xinwei; Throckmorton, Amy L. Untaroiu, Alexandrina Patel, Sonna; Allaire, Paul E.; Wood, Houston G. Olsen, Don B. (2003) Axial Flow Blood Pumps. ASAIO Journal: July 2003-Volume 49-pp 355-364.

Sutherland, K (2010) Bridging the quality gap: heart failure. The Health Foundation (Pub)

Urdaneta M G, Delille, R., Smela E. (2007) Stretchable Electrodes with High Conductivity and Photo Patternability Advanced materials, Volume 19, Issue 18, pp. 2629-2633, September 2007.

Yuan, W., Hu, L., Ha, S., Lam T. Cruner G, Pei Q (2008) Self Clearable Carbon Nanotube Electrodes for Improved performance of Dielectric Elastomer Actuators. EAPAD Proc of SPIE Vol 6927. Bar-Cohen J. Ed.

U.S. Pat. No. 6,210,318
EP 0192574
U.S. Pat. No. 4,697,574
WO 02/24255
WO 2004/045677
U.S. Pat. No. 4,733,652
U.S. Pat. No. 6,030,335
U.S. Pat. No. 4,195,623
U.S. Pat. No. 4,015,590

What is claimed is:

1. An actuator comprising:
an inner tubular structure; and
an outer tubular structure surrounding the inner tubular structure;
wherein:
the outer tubular structure comprises a plurality of layers of a dielectric elastomeric material;
the outer tubular structure comprises a tubular elastic support structure;
the tubular elastic support structure is configured to maintain a pre-stress in the plurality of layers of the dielectric elastomeric material;
the outer tubular structure is configured to contract in a radial direction around the inner tubular structure upon application of an actuation voltage signal across the dielectric elastomeric material layers; and
the tubular elastic support structure comprises an auxetic structure configured such that a ratio between expansion in the circumferential direction and contraction in the axial direction of the tubular elastic support structure when unconstrained is zero or negative.

2. The actuator of claim 1 wherein the inner tubular structure is a braided tubular structure.

3. An implantable device comprising the actuator according to claim 1 and an electronic controller configured to apply the actuation voltage signal to the plurality of layers of the dielectric elastomeric material.

* * * * *